United States Patent
Fazekas et al.

(10) Patent No.: US 8,314,249 B2
(45) Date of Patent: Nov. 20, 2012

(54) PROCESS FOR THE PREPARATION OF [4-(2-CHLORO-4-METHOXY-5-METHYLPHENYL)-5-METHYL-THIAZOLO-2-YL]-[2-CYCLOPROPYL-1-(3-FLUORO-4-METHYLPHENYL

(75) Inventors: Janos Fazekas, Budapest (HU); Peter Miskolczi, Budapest (HU); Annamaria Molnar, Budapest (HU); Bela Agai, Budapest (HU); Zsolt Parkanyi, Budapest (HU)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/282,721

(22) Filed: Oct. 27, 2011

(65) Prior Publication Data

US 2012/0083608 A1    Apr. 5, 2012

Related U.S. Application Data

(63) Continuation of application No. PCT/HU2010/000047, filed on Apr. 26, 2010.

(30) Foreign Application Priority Data

Apr. 30, 2009 (HU) .................................. 0900267

(51) Int. Cl.
C07D 277/42 (2006.01)
C07D 327/04 (2006.01)
C07D 331/04 (2006.01)

(52) U.S. Cl. .............................. 548/190; 549/30; 558/12
(58) Field of Classification Search ..................... 558/12; 549/30
See application file for complete search history.

(56) References Cited

U.S. PATENT DOCUMENTS

| 3,222,248 A | 12/1965 | Lukes et al. |
| 3,433,803 A | 3/1969 | Ottmann et al. |
| 6,586,456 B1 | 7/2003 | Fontaine et al. |

FOREIGN PATENT DOCUMENTS

| GB | 823251 | 11/1959 |
| JP | 10036360 | 2/1998 |
| WO | WO 93/09107 A1 | 5/1993 |
| WO | WO 01/05776 A1 | 1/2001 |
| WO | WO 2010/125414 A1 | 11/2010 |

OTHER PUBLICATIONS

Prakash, et al., Organoiodine(III) Mediated One-Pot Synthesis of N-Substituted 2-Aminothiazoles, J. Indian Chem. Soc., vol. 81, (2004), pp. 786-788.

Asanuma, et al., Preparation of 2-Chloro-5-Chloromethyl-1,3-Thiazole Useful as Agrochemical Intermediate—by Reaction of 3-Chloro-1-Isothiocyanato-1-Propene With a Chlorinating Agent or by Rearranging 3-Chloro-1-Thiacyanato-2-Propene in the Presence of a Metal Salt, JP abstract of application No. 1997-450613—Publication No. 7010036360, 1998.

Kamal, et al., A Task-Specific Ionic Liquid [Bmim]SCN for the Conversion of Alkyl Halides to Alkyl Thiocyanates at Room Temperature, Tetrahedron Letters, vol. 46, (2005), pp. 1489-1491.

Kiasat, et al., A Facile and Convenient Method for Syntheis of Alkyl Thiocyanates Under Homogeneous Phase Transfer Catalyst Conditions, Chinese Chemical Letters, vol. 19, (2008), pp. 1301-1304.

Merijanian, et al., Steric Effects of Ortho Substituents on Acid-Catalyzed Cyclization of Thiocyanatoacetophenones, J. Org. Chem., (1986), vol. 51, pp. 543-545.

Pihlaja, et al., A Correlative IR, MS, 1H, 13C and 15N NMR and Theoretical Study of 4-Arylthiazol-2-(3H)-Ones, J. Chem. Soc. Perkin Trans. 2, (2002), pp. 329-336.

Lempert, Szerves Kemia, Muszaki Konyvkiado. Budapest. (1976), pp. 828-829.

Lempert, Szervas Kemia, Muszaki Konyvkiado. Budapest. (1976), pp. 828-829, English Translation.

*Primary Examiner* — Laura L. Stockton
(74) *Attorney, Agent, or Firm* — Ronald G. Ort

(57) ABSTRACT

The present invention is a process for the preparation of [4-(2-chloro-4-methoxy-5-methylphenyl)-5-methyl-thiazolo-2-yl]-[2-cyclopropyl-1-(3-fluoro-4-methylphenyl)-ethyl]-amine as set forth in formula (I)

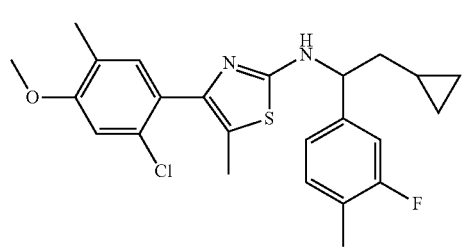

and new intermediates of the preparation process.

13 Claims, No Drawings

PROCESS FOR THE PREPARATION OF [4-(2-CHLORO-4-METHOXY-5-METHYLPHENYL)-5-METHYL-THIAZOLO-2-YL]-[2-CYCLOPROPYL-1-(3-FLUORO-4-METHYLPHENYL

The subject of the present invention is a novel process for the preparation of [4-(2-chloro-4-methoxy-5-methylphenyl)-5-methyl-thiazolo-2-yl]-[2-cyclopropyl-1-(3-fluoro-4-methylphenyl)-ethyl]-amine of formula (I)

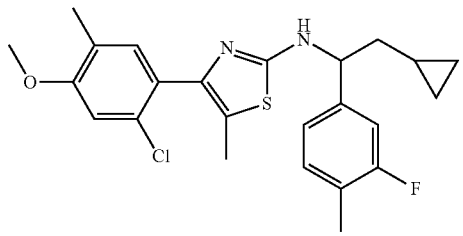

and new intermediates of the preparation process.

The compound of formula (I) is a key intermediate to the preparation of [4-(2-chloro-4-methoxy-5-methylphenyl)-N-propynyl-5-methyl-thiazolo-2-yl]-[2-cyclopropyl-1-(3-fluoro-4-methylphenyl)-ethyl]-amine of formula (VI)

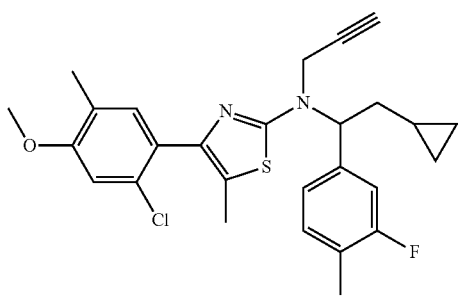

which is a known CRF1 (corticotropin releasing factor 1) receptor antagonist with potential antidepressant and/or anxiolytic effect.

The thiazolamine of formula (I) is presently prepared in several steps, utilizing the Hantzsch synthesis (WO2001/005776, Sanofi-Aventis).

The preparation process used so far (WO2001/005776, Sanofi-Aventis) starts from the compound of formula (II)

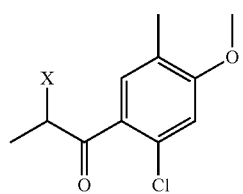

where X means halogen atom. This compound, however, easily decomposes, it is irritative, its quality is hard to reproduce, and its isolation and treatment involves difficulties.

Our aim was to find a starting material for the preparation of the compound of formula (I) which is well characterized, easy to treat, which is well crystallizable, and can be prepared conveniently, in high yield. To our surprise, we found that 2-thiocyanato-1-(2-chloro-4-methoxy-5-methylphenyl)-propan-1-one of formula (III)

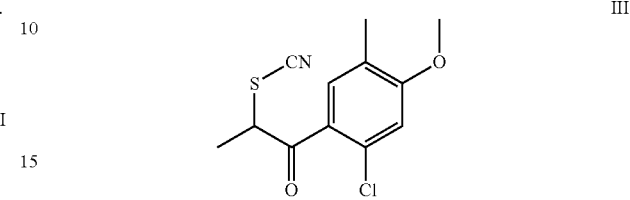

is a starting material which fulfills all our needs. A further advantage of applying the compound of formula (III) is that under specific conditions, i.e. in the presence of a phase transfer catalyst, it can be prepared easily in aqueous medium, from the previously used compound of general formula (II). This new process according to our invention is environment friendly, since only aqueous effluent is formed, the amount of the used organic solvents is small and the solvents can be re-used, the process can be performed in industrial scale and it results high purity product in high yield.

The preparation of the ketone derivative (III) in aqueous conditions is surprising, since the thiocyanate group is sensitive to water, it can easily transform into isothiocyanate, or it can suffer hydrolysis. Therefore, in the state of art, it is prepared either in ionic liquid (Tetrahedron Letters 46 (2005), 1489-1491) or in alcoholic medium (J. Indian Chem. Soc., 81 (2004), 786-788), but in any case in the absence of water.

A subject of the invention is a novel process for the preparation of [4-(2-chloro-4-methoxy-5-methylphenyl)-5-methyl-thiazolo-2-yl]-[2-cyclopropyl-1-(3-fluoro-4-methylphenyl)-ethyl]-amine of formula (I)

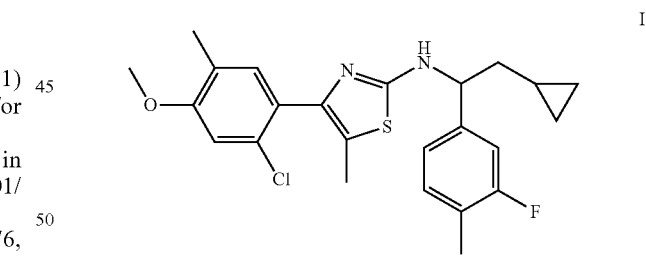

wherein
a.) the 2-halogeno-1-(2-chloro-4-methoxy-5-methylphenyl)-propan-1-one of the general formula (II)

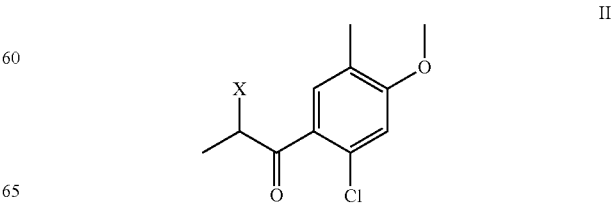

where X means halogen, is reacted with an alkali metal-thiocyanate, in the presence of a phase-transfer catalyst, and b.) the thus obtained 2-thiocyanato-1-(2-chloro-4-methoxy-5-methylphenyl)-propan-1-one of formula (III)

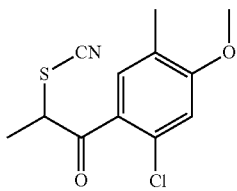

III or a tautomeric form of it is reacted with the 2-cyclopropyl-1-(3-fluoro-4-methylphenyl)-ethyl-amine

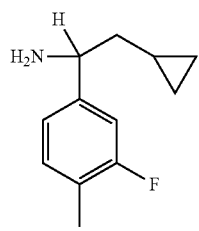

IV of formula (IV).

To prepare the appropriate optically active isomer of the compound of formula (I) we have to start from the respective optically active amine of formula (IV).

In one embodiment of the process according to the invention, in step a.) the reaction is performed in the binary system consisting of an aprotic solvent and water.

In one alternative of the process according to the invention, the compound of the general formula (II)—where X is particularly a chloro or bromo group, more particularly a bromo group,—is dissolved in an aprotic organic solvent and reacted with the aqueous solution of an alkali metal-thiocyanate—preferably potassium-thiocyanate—in the presence of a phase transfer catalyst—preferably TBAB (tetrabutyl-ammonium bromide). The reaction mixture is worked-up by separation of the organic phase after dilution of the mixture with water. In a given case after solvent exchange, the compound of the formula (III) can be well crystallized, in high yield.

In one variant of step b.) the compound of formula (III) is added to the compound of formula (IV), to obtain the desired product with a favorable impurity profile and in high yield.

To achieve the best yield the addition period lasts for at least one hour.

In step b.) favorably an apolar aprotic solvent is applied, preferably methyl-cyclohexane or toluene. Step b.) is preferably performed at a temperature range between 25° C. and reflux temperature, most preferably at reflux temperature.

The compounds of the general formula (II) and the amine of formula (IV), as well as their preparation are known from the patent application of publication number WO2001/005776.

A further subject of the invention is the new compound of formula (III) and its tautomers, as well as their preparation.

Of the tautomers of compound (III), the 5-(2-chloro-4-methoxy-5-methylphenyl)-4-methyl-[1.3]-oxathiol-2-ylideneamine of formula (V)

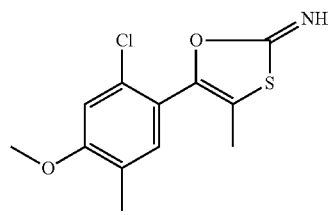

V is also a subject of the invention.

Further details of our process are demonstrated in the following examples without limiting the claims to the examples.

EXAMPLES

Example 1

Preparation of Compound (III) From Compound (II) in Dichloromethane (DCM)

291.5 g 2-bromo-1-(2-chloro-4-methoxy-5-methylphenyl)-propan-1-one (II) is dissolved in 291 g DCM, 5.3 g TBAB (tetrabutyl-ammonium-bromide) catalyst is added to it.

167 g KSCN is dissolved in 83.6 g water. The aqueous solution is added to the DCM solution.

The resulting binary system is heated to 40° C. (reflux) and is stirred for 3-4 hours.

The reaction is accompanied by salt precipitation. Water is added to the mixture until the salt dissolves. The lower, aqueous phase is separated, the upper, organic phase is evaporated, while 870 ml methanol (MeOH) is added to it.

From the methanol solution compound (III) crystallizes on cooling. The crystals are filtered off, washed several times with MeOH.

Yield: 90-95%

Melting point: 75° C. (MeOH)

IR-spectrum: 2158 cm$^{-1}$ (CN), 1664 cm$^{-1}$ (C=O)

$^1$H-spectrum (DMSO-$d_6$, TMS): 7.73 (1H, s), 7.14 (1H, s), 5.28 (1H, q, J=7, 2Hz), 3.89 (3H, s), 2.16 (3H, s), 1.60 (3H, d, J=7.2 Hz)

$^{13}$C-NMR-spectrum: 194.7, 160.9, 132.6, 131.5, 126.3, 125.5, 113.5, 111.4, 56.7, 49.4, 18.8, 15.8

Example 2

Preparation of Compound (III) From Compound (II) in Methyl-Cyclohexane (MCH)

The preparation procedure is as described in Example 1, but MCH is used as solvent, instead of DCM. The product is crystallized from MCH on cooling.

Yield: 60%

Example 3

Preparation of Compound (V) From Compound (III) in an Apolar Solvent in the Presence of an Amine 26.4 g compound (III) (prepared as described in example 1. or 2.) is suspended in
52 ml MCH.
In stoichiometric amount an amine (preferably benzylamine) is added to the mixture.
The mixture is stirred for 0.5-1 hour (the structure of the amine influences the reaction time). Thick precipitate is obtained, it is filtered off and washed several times with methyl-cyclohexane.
Yield: 85%.

Example 4

Preparation of Compound (V) From Compound (III) in a Tertiary Amine as Solvent The preparation procedure is as described in Example 3, with the difference that compound (III) is suspended in triethyl-amine as solvent, instead of MCH, and no other amine is added to the mixture.
Yield: 85%
Melting point: 106° C. (EtOH)
IR-spectrum: 3253 $cm^{-1}$ (NH), 1679 $cm^{-1}$ (C=N)
$^1$H-spectrum (DMSO-$d_6$, TMS): 7.30 (1H, s), 7.14 (1H, s), 3.86 (3H, s), 2.14 (3H, s), 1.88 (3H, s)
$^{13}$C-NMR-spectrum: 163.1 (s), 158.9 (s), 138.9 (d), 133.0 (s), 131.4 (s), 125.3 (s), 118.3 (s), 111.8 (d), 111.5 (s), 56.0 (t), 15.3 (t), 11.6 (t)

Example 5

Preparation of Compound (I) From Compound (III) in Methyl-Cyclohexane (MCH)

26.3 g isolated product (III) is dissolved in
52 ml MCH.
The reaction mixture is heated to 85-90° C. and is added to the 85-90° C. solution of
19.2 g amine (IV) in MCH (20%). The addition period is 2-4 hours. After the addition, the reaction mixture is stirred at 85-90° C. for one hour. The MCH solution of the crude product (I) is cooled and the precipitated crystals are filtered off. The crystalline product is covered with a small amount of MCH.
Yield: 80%.

Example 6

Preparation of Compound (I) From Compound (III) in MCH and MeOH

The preparation procedure is as described in Example 5, but product (I) is crystallized from MeOH, instead of MCH, after solvent exchange.
Yield: 90%.

Example 7

Preparation of Compound (I) From Compound (V)

The preparation procedure is as described in Examples 5 and 6, but instead of compound (III), compound (V) is used, in the same amount.

Yield: 85%.

We claim:

1. A process for the preparation of [4-(2-chloro-4-methoxy-5-methylphenyl)-5-methyl-thiazolo-2-yl]-[2-cyclopropyl-1-(3-fluoro-4-methylphenyl)-ethyl]-amine of formula (I)

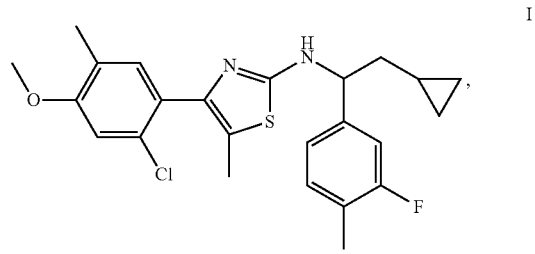

the process comprising a.) reacting a compound of formula (II)

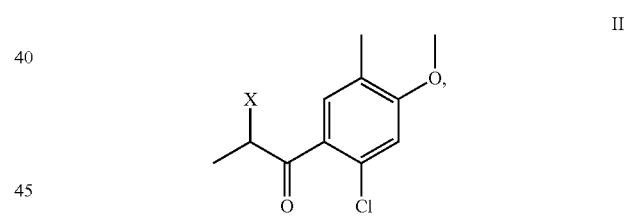

wherein X represents a halogen, with an alkali metal-thiocyanate, in the presence of a phase transfer catalyst, to obtain a 2-thiocyanato-1-(2-chloro-4-methoxy -5-methylphenyl)-propan-1-one of formula (III)

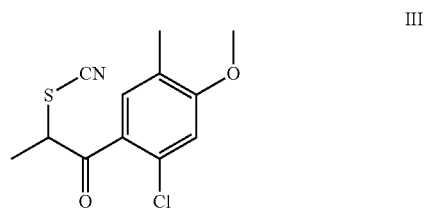

or a tautomeric form thereof; and b) reacting said compound of formula (III) or tautomeric form thereof with 2-cyclopropyl-1-(3-fluoro-4-methylphenyl)-ethyl-amine of formula (IV)

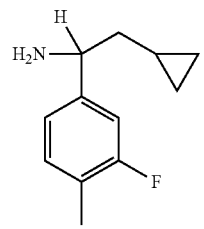

to form the compound of formula (I).

2. The process as defined in claim 1, wherein in step b) the compound of formula (III) is added to the compound of formula (IV).

3. The process as defined in claim 2, wherein the addition of the compound of formula (III) to the compound of formula (IV) takes at least 1 hour.

4. The process as defined in claim 1, wherein the reaction of step a) is performed in a binary system consisting of an aprotic solvent and water.

5. The process as defined in claim 1, wherein the reaction of step b) is carried out in an apolar aprotic solvent.

6. The process as defined in claim 5, wherein the apolar aprotic solvent is methyl-cyclohexane or toluene.

7. The process as defined in claim 1, wherein the reaction of step b) is carried out at a temperature between 25° C. and reflux temperature, inclusively.

8. The process as defined in claim 7, wherein the reaction of step b) is carried out at reflux temperature.

9. The process as defined in claim 1, wherein in formula (II) X is bromine.

10. A 2-thiocyanato-1-(2-chloro-4-methoxy-5-methylphenyl)-propan-1-one of formula (III)

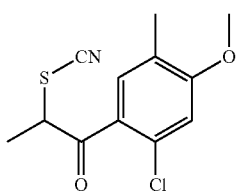

or a tautomer thereof.

11. A compound of formula (III) according to claim 10 in the form of a tautomer, which is 5-(2-chloro-4-methoxy-5-methylphenyl)-4-methyl-[1.3]-oxathiol-2-ylidene-amine of formula (V)

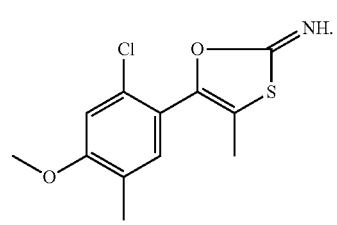

12. A process for the preparation of 2-thiocyanato-1-(2-chloro-4-methoxy-5-methylphenyl)-propan-1-one of formula (III)

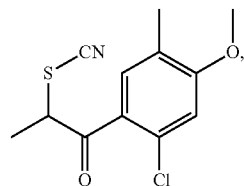

the process comprising reacting a compound of formula (II)

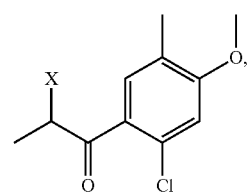

where X represents a halogen, with an alkali metal-thiocyanate, in the presence of a phase transfer catalyst.

13. A process for the preparation of [4-(2-chloro-4-methoxy-5-methylphenyl)-5-methyl-thiazol-2-yl]-[2-cyclopropyl-1-(3-fluoro-4-methyl-phenyl)-ethyl]-amine of formula (I)

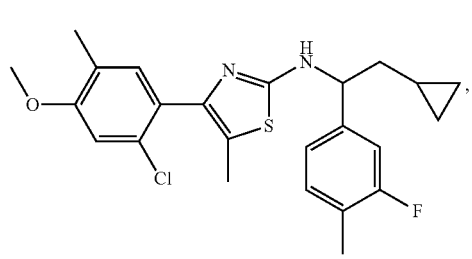

the process comprising reacting 2-thiocyanato-1-(2-chloro-4-methoxy-5-methyl-phenyl)-propan-1-one of formula (III)

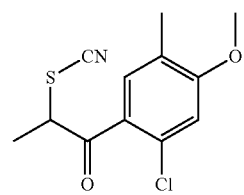

with 2-cyclopropyl-1-(3-fluoro-4-methylphenyl)-ethylamine of formula (IV)

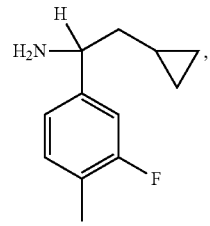

wherein the compound of formula (III) is added to the compound of formula (IV).

* * * * *